United States Patent
Duncan et al.

(10) Patent No.: US 10,456,116 B2
(45) Date of Patent: Oct. 29, 2019

(54) SHADOW SUPPRESSION IN ULTRASOUND IMAGING

(71) Applicant: Siemens Medical Solutions USA, Inc., Malvern, PA (US)

(72) Inventors: David P. Duncan, Renton, WA (US); Manoj G. Menon, Bellevue, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 461 days.

(21) Appl. No.: 14/501,482

(22) Filed: Sep. 30, 2014

(65) Prior Publication Data

US 2016/0089116 A1    Mar. 31, 2016

(51) Int. Cl.
| A61B 8/08 | (2006.01) |
| A61B 8/13 | (2006.01) |
| G01S 15/89 | (2006.01) |
| G01S 7/52 | (2006.01) |
| A61B 5/00 | (2006.01) |

(52) U.S. Cl.
CPC .............. *A61B 8/5269* (2013.01); *A61B 8/13* (2013.01); *A61B 8/5207* (2013.01); *A61B 8/5253* (2013.01); *G01S 7/52033* (2013.01); *G01S 15/8977* (2013.01); *G01S 15/8995* (2013.01); *A61B 5/7257* (2013.01)

(58) Field of Classification Search
CPC ........... A61B 8/00; A61B 8/5269; A61B 8/13; A61B 8/145; A61B 8/5207; A61B 8/5253; G01S 15/8977; G01S 15/8995; G06T 7/0012
See application file for complete search history.

(56) References Cited

U.S. PATENT DOCUMENTS

| 5,779,641 | A  | * | 7/1998 | Hatfield | ................... A61B 8/06 128/916 |
| 6,527,720 | B1 | * | 3/2003 | Ustuner | ............... A61B 8/0858 600/443 |
| 6,858,010 | B2 |   | 2/2005 | Guracar et al. | |
| 6,911,008 | B2 |   | 6/2005 | Pelissier | |
| 7,104,957 | B2 |   | 9/2006 | Miller | |
| 7,519,412 | B2 |   | 4/2009 | Mistretta | |
| 8,170,315 | B2 |   | 5/2012 | Mistretta | |
| 8,233,682 | B2 |   | 7/2012 | Fessler | |
| 9,498,189 | B2 |   | 11/2016 | Taniguchi et al. | |
| 2007/0276237 | A1 | * | 11/2007 | Li | ....................... G01S 7/52095 600/437 |

(Continued)

FOREIGN PATENT DOCUMENTS

| CN | 101248458 A | 8/2008 |
| DE | 102010047155 A1 | 5/2011 |
| JP | 2010029281 | 2/2010 |

*Primary Examiner* — Carolyn A Pehlke

(57) ABSTRACT

Shadow suppression is provided in ultrasound imaging, such as in steered spatial compounding. Using a transform or other approach, the data of a frame of data along the steering direction is projected. The projection is used to determine weights. The frame is weighted with the projection-based weights, reducing or removing shadows based on the one frame rather than based on registration with other frames. In the steered spatial compounding example, a compounded frame with independently shadow suppressed component frames may have little or no fork-like image artifacts due to shadowing.

19 Claims, 6 Drawing Sheets

(56) References Cited

U.S. PATENT DOCUMENTS

| | | | |
|---|---|---|---|
| 2008/0033288 A1* | 2/2008 | Wang | A61B 8/0825 |
| | | | 600/427 |
| 2009/0129651 A1* | 5/2009 | Zagzebski | G01S 7/52046 |
| | | | 382/131 |
| 2010/0160783 A1 | 6/2010 | Halmann | |
| 2011/0054323 A1* | 3/2011 | Ahn | G01S 7/52034 |
| | | | 600/443 |
| 2013/0053687 A1* | 2/2013 | Lin | A61B 8/0841 |
| | | | 600/424 |
| 2013/0208965 A1 | 8/2013 | Sui et al. | |
| 2013/0294665 A1* | 11/2013 | Rao | G01S 15/8977 |
| | | | 382/131 |
| 2014/0343420 A1* | 11/2014 | Zhang | A61B 8/0825 |
| | | | 600/437 |
| 2015/0293222 A1* | 10/2015 | Huang | G01S 15/8977 |
| | | | 367/7 |

* cited by examiner

SHADOW SUPPRESSION IN ULTRASOUND IMAGING

BACKGROUND

The present invention relates to shadow suppression in ultrasound imaging.

Ultrasound shadowing is caused by poor transmission of acoustic energy through or high reflection from scattering objects. For example, dense tissue may cause a shadow obscuring return from tissue separated from the transducer by the dense tissue. As another example, shadowing occurs due to poor transducer contact. The shadows themselves appear as areas of low echogenicity that are typically highly correlated with the direction of transmission.

Shadows may occur in various modes of imaging, such as occurring in steered spatial compounding. One component frame of data is acquired by scanning along scan lines at one angle relative to a transducer. A second component frame of data is acquired by scanning along scan lines at a different angle. The frames of detected data are compounded together and displayed as an image. When imaging using steered spatial compounding, shadows create fork-like image artifacts since the shadows tend to weigh down the compounded image mean in the shadowing locations. Anatomy information may be lost due to this reduction. For reducing shadowing in steered spatial compounding, differences between steered spatial component images may be used to identify shadows. However, proper spatial image registration may not be achieved, resulting in poor shadow identification.

BRIEF SUMMARY

By way of introduction, the preferred embodiments described below include methods, computer readable media, instructions, and systems for shadow suppression in ultrasound imaging. Using a transform or other approach, the data of a frame (e.g., image frame) along the steering direction is projected. The projection is used to determine weights. The frame is weighted with the projection-based weights, reducing or removing shadows based on the one frame itself. In the steered spatial compounding example, a compounded frame with independently shadow suppressed component frames may have little or no fork-like image artifacts due to shadowing.

In a first aspect, a method is provided for shadow suppression in ultrasound imaging. A transducer is used to acquire steered component frames of data. The steered component frames of data represent an overlap region of a patient and being responsive to different imaging angles. For the steered component frames of data, a processor projects the data along the respective imaging angles into projections. The steered component frames of data are weighted by kernels that are a function of the respective projections. The processor compounds the weighted component frames of data together. An image of the overlap region of the patient is generated from a result of the compounding.

In a second aspect, a non-transitory computer readable storage medium has stored therein data representing instructions executable by a programmed processor for shadow suppression in ultrasound imaging. The storage medium includes instructions for steered spatial compounding component frames, by an ultrasound system, for ultrasound imaging; and reducing shadows, by the ultrasound system, in at least one of the component frames independently the others of the component frames.

In a third aspect, a system is provided for shadow suppression in ultrasound imaging. A beamformer is operable to acquire a sequence of steered frames of data responsive to different steering angles from a substantially same transducer position and representing an overlap region. A processor is configured to project the steered frames of data along the steering angles into projection images, weight the steered frames of data as a function of the projection images, and generate a compound image from the weighted steered frames of data. A display is operable to display the compound image.

Further aspects and advantages of the invention are discussed below in conjunction with the preferred embodiments. The present invention is defined by the following claims, and nothing in this section should be taken as a limitation on those claims.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION

The received image data of a single frame is transformed, and a projection image is generated using knowledge of the transmit imaging angle. The transformed projection image is then used to generate weights. Knowledge of the transmit angle direction and corresponding transform projection images are used to help determine the steered spatial compounding image weights. The weights are used to compensate the original received image data. This approach does not require image registration for shadow reduction as shadows are suppressed by weighting the original images using their respective projection images. The shadow reduction weights are created on a per frame basis even for steered compounding.

Figure 1:
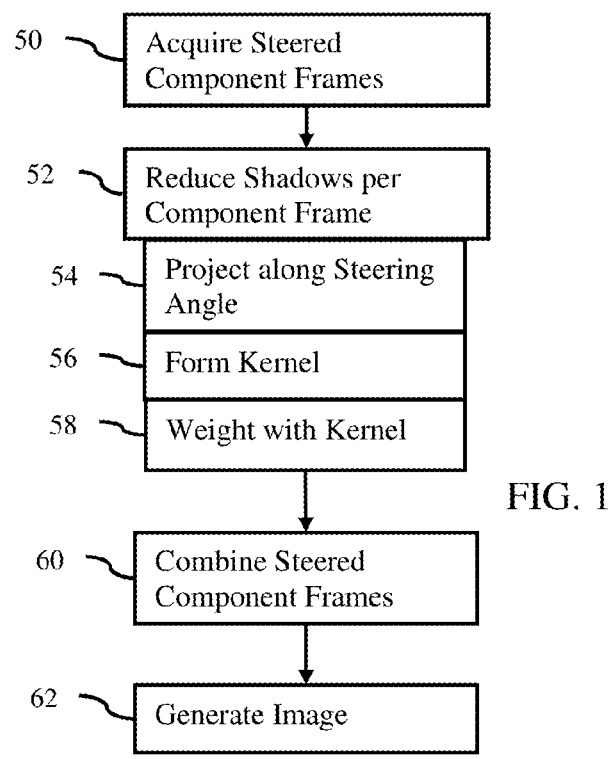
FIG. 1 is a flow chart diagram of one embodiment of a method for shadow suppression in ultrasound imaging.

FIG. 1 shows one embodiment of a method for shadow suppression in ultrasound imaging. The embodiments are described below in the context of steered spatial compounding. In other embodiments, shadow suppression is provided for single or multiple frame imaging modalities, such as B-mode imaging.

Figure 10:
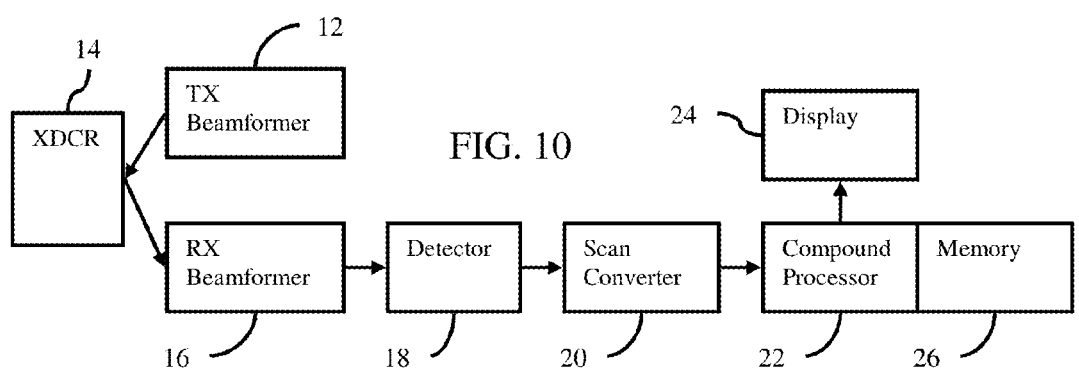
FIG. 10 is a block diagram of a system for shadow suppression in ultrasound imaging, according to one embodiment.

The method is performed by the system of FIG. 10 or a different system. A medical diagnostic ultrasound imaging system may perform the method, such as using a transducer and beamformer to scan the patient at different steering angles, a detector (e.g., B-mode detector) to detect data for frames of data, a processor to suppress shadow and compound the component frames of data into a compound frame of data, and a display to display an image created from the compound frame of data. Other systems may be used, such as a computer for receiving component frames and outputting a compound frame with reduced shadow.

The method is performed in the order shown or a different order. Additional, different, or fewer acts may be provided. For example, act 56 is not performed where the projection of act 54 itself provides the weights of the kernel. As another example, act 62 is not performed. In yet another example, further processing, such as detecting and scan converting, is provided.

Figure 2:
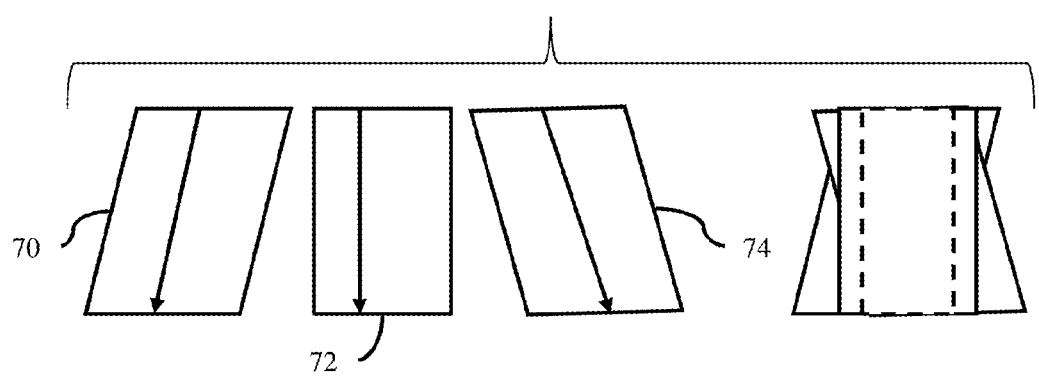
FIG. 2 is an example representation of three steered component frames of data.

In act 50, component frames of data are acquired with ultrasound using a transducer. The component frames of data have a different spatial response. The component frames of data are steered electrically, mechanically, or by spatial positioning of the transducer. Each or multiple of the steered component frames of data are acquired at different steering angles. For example, FIG. 2 shows three electronically steered frames 70, 72, and 74 of data acquired in response to three different steering angles (see the ray line for each frame 70, 72, 74) or scan patterns with one or more scan lines at a different steering angle. Each of the component frames of data span substantially a same spatial extent of a region of a target, such by maintaining the transducer in a same position with or without intentional wobbling. A majority, above 90% or almost the entire scanned region for each of the component frames of data overlaps with the scanned regions of the other component frames (see the dashed box).

One of the component frames of data is responsive to at least one different scan line angle relative to at least one location in the scanned region than another of the component frames of data. For at least some locations in the patient, the intersecting scan lines from the different component frames are at different angles, at least for two of the component frames. Insonifying the location from different directions provides different spatial response.

In alternative embodiments, the transducer is moved during acquisition of sequential frames of data, such as associated with extended field of view imaging. Where non-linear scan patterns are used, where the transducer is rotated as well as translated, or where multiple transducers are spatially positioned to acquire the target images, different component frames of data may represent overlapping regions from different angles, providing different spatial response. By combining the data for the overlapping regions, steered compounding is provided.

Two or more frames of data are acquired representing the same or different regions. For example, the scan lines of three component frames of data are each associated with a different region or scan geometry. The scan lines may be acquired in any format, such as linear, curved linear, sector curved sector, Vector®, curved Vector® and combinations thereof. For example, scan lines acquired with a linear transducer are steered at three different angles (e.g., +/−10 degrees and normal) in a linear or generally rectangular or parallelogram scan format for three component frames of data, respectively.

For one component frame of data, the scan lines originate at different positions on the transducer, but two or more scan lines may originate from a same position. Using the linear format, the scan lines are parallel and in a same direction relative to the intersections of the scan lines with the origins on the transducer. The majority of the scan lines of each component frame point in a same direction. As another example, different angles from the face of the transducer 14 are provided by a scanning apex position on or behind the transducer 14 for sector or Vector® formats. The scan line density along the transducer surface is either uniform or changes as a function of the scan line position. The scan line density may be different for one frame of data as compared to another frame of data, such as having different uniform densities or having differences in variation of the density. Any of various combinations of formats or variation in scan line origin or angle within a single scan or between scans resulting in spatial diversity may be used.

Each of the component frames of data corresponds to different steering angles or spatial response. For example, a majority of scan lines extend in a first direction, such as 10 degrees left from the transducer for one component frame of data. The majority of scan lines extend at a 10 degree right angle from the transducer for another component frame of data. The majority of the scan lines are normal to the transducer for a third component frame of data. Different steering angles other than plus or minus 10 degrees and zero may be used with 2, 3, 4 or more component frames.

In one embodiment, one component frame is associated with the maximum angle of steering provided by the transducer without undesired grating lobe effects. A second component frame is associated with the same angle but in a different direction relative to the transducer. Additional component frames, if any, are associated with lesser angles of steering. In alternative embodiments, the greatest steering angle is less than the maximum possible with the transducer. As another example, the position of the scanning apex of the scan lines is different, such as spaced laterally, between two component frames of data, resulting in different steering angles. As yet another example, the scan lines are steered the same for each component frame of data, but the transducer is wobbled about an axis, such as the azimuth axis.

In one embodiment, the same or substantially same scan lines are used for both transmit and receive operations for any given component frame of data. In alternative embodiments, one or more of the scan lines are different for transmit than for receive operation. For example, acoustic energy is transmitted along scan lines normal to the transducer for a linear array and received along scan lines at non-normal angles. For a curved array, the energy is transmitted along scan lines in one format and received along scan lines in a different format, pattern or positions. As another example, the same scan lines are used for transmit for all or multiple of the component frames of data, but different electric steering is provided during receive of each or multiple of the component frames of data.

Each frame of data is formed of samples representing the field of view or scanned region. The frame may be for a two or three-dimensional region. Different frames may be acquired in an interleaved manner, such as acquiring by lines or groups of lines for one frame interleaved with lines or groups of lines for another frame.

Figure 3:
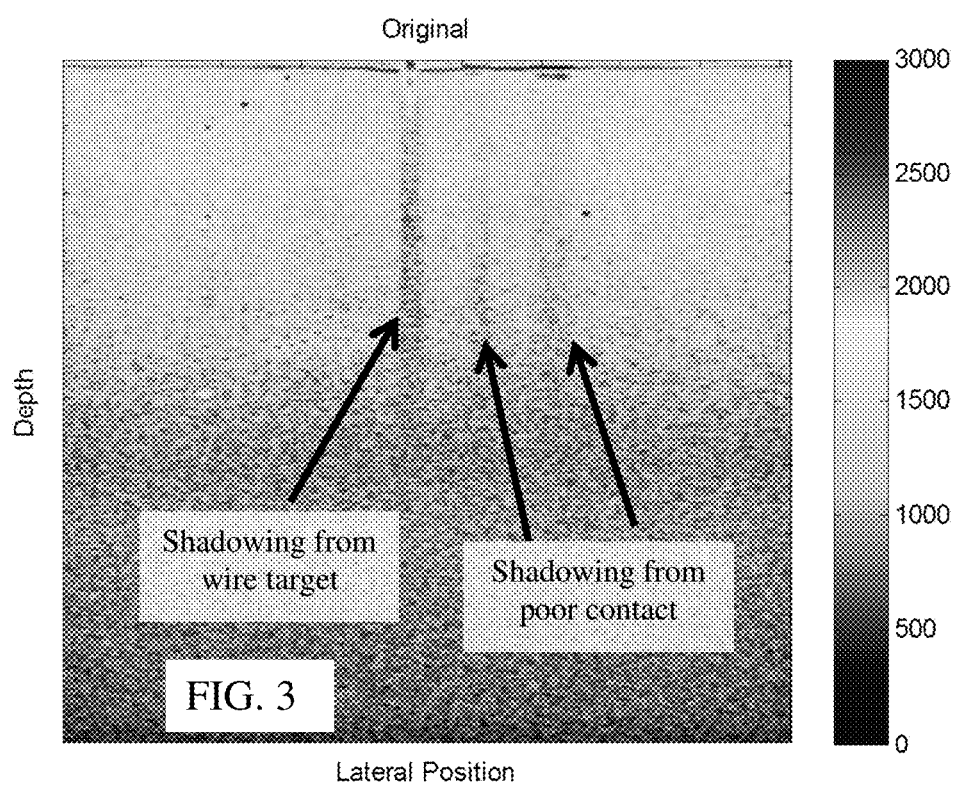
FIG. 3 is an example ultrasound image with shadowing.

One or more, such as all, of the component frames may include shadowing artifact. The data, if used to generate an image, includes shadowing. FIG. 3 shows an example of shadowing in a frame of data acquired using a linear scan pattern (i.e., all steering angles the same for the entire frame). Ultrasound from a transducer is used to scan a region of a phantom or patient. The phantom image of FIG. 3, shown here with log-compressed or B-mode data mapped to color, demonstrates the effects of various types of shadowing. In this instance, the darkest shadow is caused by a wire target placed at the phantom surface between the phantom and the transducer, while the other two shadows are caused by suboptimal transducer contact with the phantom. Air or other interfering material cause attenuation or scattering greater than other soft tissue, so result in less or lower intensity returns from beyond the air or other interfering material.

The shadows are along the scan lines or steering direction. In the example of FIG. 3, a linear scan pattern is used, so the imaging or steering directions are vertical lines. The wire and poor transducer contacts result in reduced return along three vertical lines or groups of lines. The reduced acoustic return caused by shadowing is shown as darker in FIG. 3 due to color mapping used for the B-mode image.

In act 52, the shadows are reduced. The shadow reduction is performed by an ultrasound system, such as the ultrasound system used to acquire the component frames in act 50. Alternatively, a computer, processor, or other device performs the reduction.

Act 54, 56, and 58 make up act 52. Act 54 provides projection from a frame for forming the kernel in act 56. The weights making up the kernel are used to weight the frame in act 58. Additional, different, or fewer acts may be provided.

The reduction is performed independently for a given frame of data. The shadow reduction does not depend on a different frame. For example, a given frame is not registered with other frames for identifying shadows. For steered spatial compounding, the shadow reduction is performed for one or more (e.g., all) of the component frames of data. The reduction for any given component frame is performed without using other frames of data. The projecting and weighting for each of the steered component frames of data is performed independently of the other component frames of data.

In the case of steered spatial compounding, the addition of shadows in the images can create fork-like artifacts that hide detail and lead to distracting spatio-temporal variance changes. By using independent or single frame projection shadow compensation in steered spatial compounding, the artifacts from each component frame are reduced by the weighting applied to the component frame. Using frame-independent processing, if only one of the component frames of data has a large shadow, then compensating for the shadow in that frame helps to enhance the data from the other transmissions during the compounding stage.

In act 54, the data for a frame is projected along the image angle or angles for the frame. A processor performs the projection for one or more component frames of data. The data is compressed or dimension represented is reduced. The frame is collapsed along the steering or transmit direction or directions used to acquire the frame of data. Where the projection is performed for different component frames of data to be used for steered spatial compounding, the transmit angles or scan directions for each frame are different. The projection direction is different as a result.

The most significant contribution to the shadowing is the projection along the transmission direction. In the example of FIG. 3, the scan lines, transmit angle direction, and receive angle direction are vertical or along the depth dimension. To quickly and efficiently compensate for shadows in the ultrasound imagery, the data of the frame is projected to provide an indication of variation in intensity laterally or along an azimuth direction perpendicular to the depth direction.

Any projection may be used. In one embodiment, the data along each scan line or lines through the field of view that are parallel to or at the transmit angle are summed. The sum itself may be used, such that a sum is provided for each of the scan lines or other lines in a same direction as the scan lines. Alternatively, an average or other combination function is used. The result is a sum or other value for each line (e.g., each scan line), showing variation as a function of lateral direction for the two-dimensional field of view represented by the frame of data.

In another embodiment of projection, the frame of data is transformed into a k-space. The image data or frame of data is transformed into a two-dimensional frequency domain. Any transform may be used, such as a Fourier, two-dimensional Fourier, fast Fourier, or Radon transformation. Using Fourier or other frequency domain analysis, the linear nature of the shadows suggest that most of the image energy relating to shadow effects dwells along only a few lines in k-space, such as lines close to the $f_x$ axis where $f_x$ is a lateral frequency (horizontal in frequency space).

Using the transform for the projection may allow for selection of different data or information. For example, in addition to selecting data based on the scan lines, data is selected to reduce noise effects. A range of angles rather than just the steering angle may be selected (e.g., +/−5 degrees about the steering angle). This selection may reduce over compensating for the shadow at deeper depths. Any selection may be used in the frequency domain.

Figure 4:
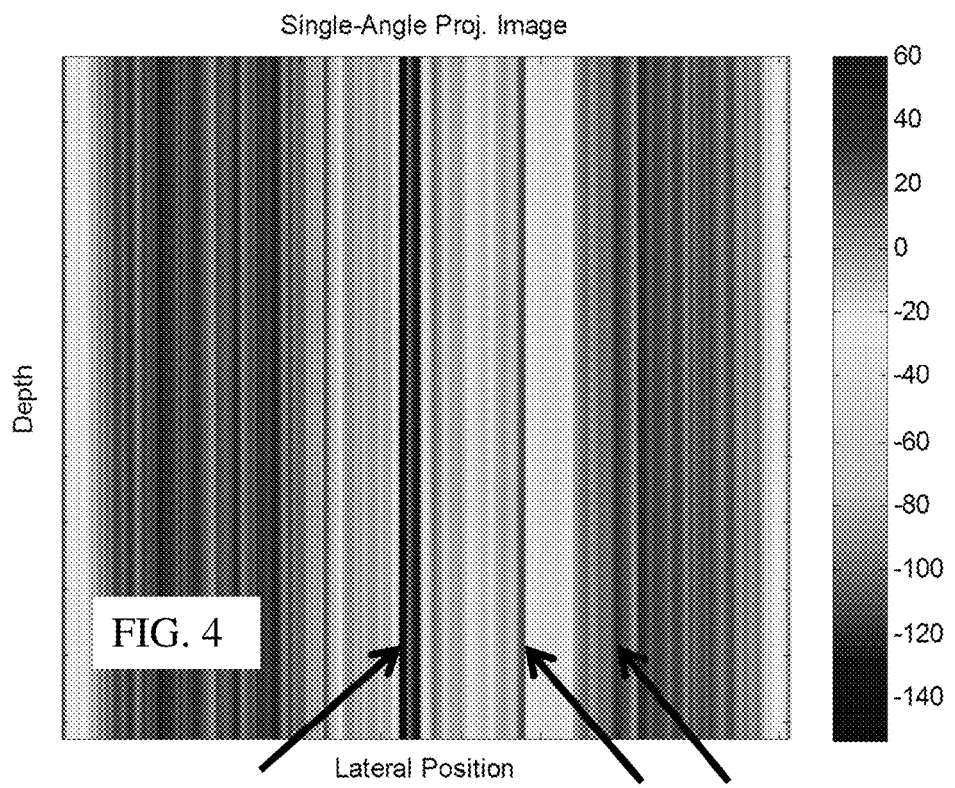
FIG. 4 is an example projection image derived from the ultrasound image of FIG. 3.

By using the transform, an inverse transform on the selected data provides information for the field of view. For example, the data related to the steering direction is inverse transformed to create a projection image. The projection image has a same spatial extent as the component frame of data, but is formed from data of the selected characteristics. The amount of shadow is represented in the projection image. FIG. 4 shows an example of a projection image created from FIG. 3 using a two-dimensional Fourier transform and selection or projection of data only along the single angle—the transmit angle. FIG. 4 is a color mapped image shown in gray scale for this disclosure. The arrows point to the lines associated with the strong shadow artifacts. Other dark lines are of different colors and not associated with shadow. Due to the projection provided by the transform, the projection image has a one-dimensional quality but expanded or extending over the two-dimensional field of view. Where other data is selected in the frequency domain, there may be less of but still some one-dimensional aspect or appearance. While projection "image" is used here, this is not a displayed image, but may be. Instead, the projection image is a frame of data created by projection.

Where the projection is performed by summing without applying a transform, the projection is then expanded along the imaging angles into a two-dimensional field. The expansion occurs prior to mapping to weights or as part of creating the weights in act 56. A projection image is created from the projection by populating each depth or range with a same lateral distribution of the projection. For example, by expanding the average projection along the vertical steering direction of FIG. 3, the projection image of FIG. 4 is provided. For each vertical line, the corresponding average along the line is assigned to all of the locations of the line.

In the projection images, the same intensity is provided along each steering direction or scan line. In other embodiments, the intensity varies as a function of depth. For example, the data selected in the frequency domain includes more than just the steering angle, causing depth dependent variation in the projection image. As another example, the projection image is altered or the expansion is adjusted so that the contribution varies as a function of depth. The deeper locations may have less shadow for surface shadow sources, so the projection image may be assigned reduced intensity as a function of depth. The inverse function may be used.

In act 56, a kernel is formed. The kernel is a collection of weights to weight the frame of data. The kernel has a weight for each of the samples or spatial locations represented in the component frame of data. Alternatively, each weight is provided for a group of locations. The weights are applied before compounding in act 60 or are applied to the component frame as part of compounding in act 60.

The weights are set to reduce the shadow artifact. The lower intensities caused by shadowing are increased and/or the higher intensities not caused by shadowing are decreased. The shadowing is reduced by more greatly equalizing the intensities or values of the frame between the shadow regions and non-shadow regions.

The kernel is formed from the projection image. The two-dimensional field of projection information is used to determine the weights. The values of the projection image are mapped to weights. In one embodiment, the mapping is 1-to-1, so the projection image itself is used as the weights. No mapping is needed as the values of the projection image are the weights. In other embodiments, any linear or non-linear mapping function may be used. For example, the dynamic range of the projection image is mapped to a smaller range of weights, such as to 1.0-1.5. The locations not associated with shadow or the highest values of the projection are mapped to 1.0. The locations associated with the strongest shadow (e.g., least intensity in the projection image) are mapped to 1.5, increasing the intensity. Other intensities in the projection image are mapped to values between 1.0 and 1.5 using any function, such as an exponential decay function. Other ranges may be used.

The weights of the kernel are specific to the component frame of data. Since the weights are determined from a projection of the component frame, information from other component frames is not used. The weights of each component frame are derived from the data of the component frame without using data from other component frames. The shadow reduction is specific to the shadowing represented in the component frame.

In act 58, the weights of the kernel are applied to the frame of data. The weights as derived from the frame are in turn applied to the frame. The weights are distributed in space over the field of view. Each location or value in the component frame is multiplied by the corresponding weight. In other embodiments, division, addition, subtraction, other functions, or combinations thereof are used to apply the weights. The application of the weights reduces the shadowing artifact.

Figure 5:
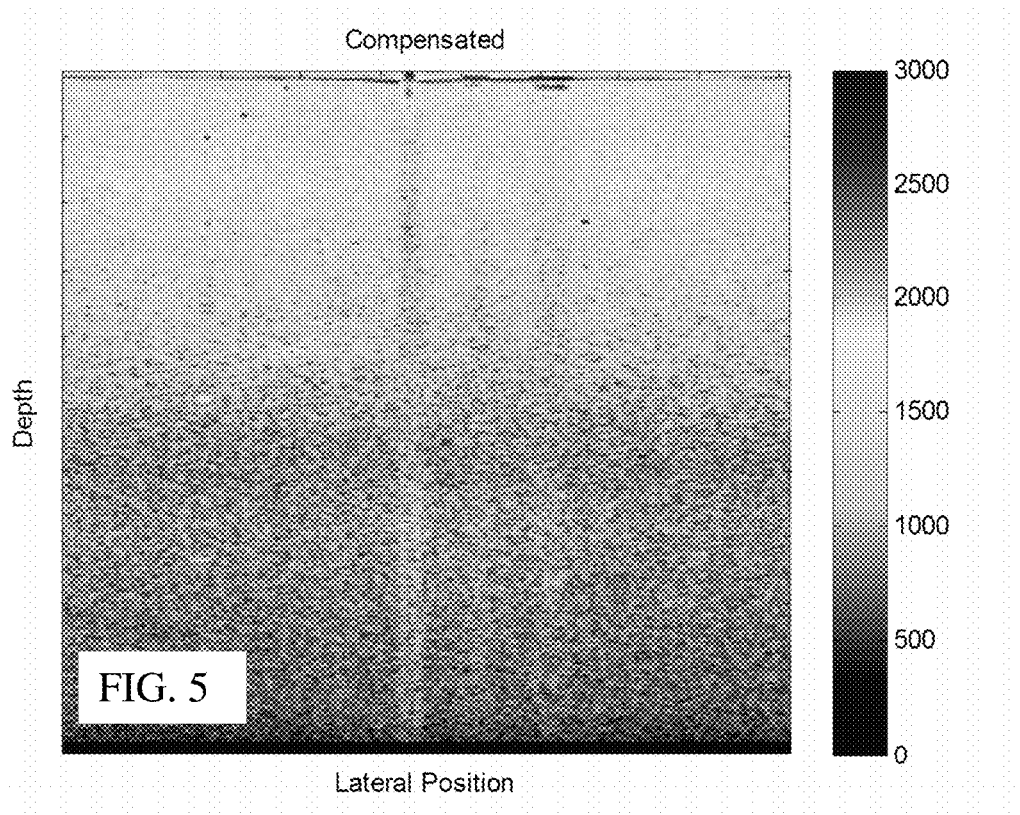
FIG. 5 is the example of ultrasound image of FIG. 3, but weighted using the projection image of FIG. 4.

FIG. 5 shows an example. The projection image of FIG. 4 is used as weights. The frame of data, as represented by FIG. 3, is weighted by the projection image of FIG. 4. The result is the weighted frame of data represented in FIG. 5. The visibility or magnitude of the shadowing artifact is reduced. In this example, the single angle projection greatly reduces the effect of the shadowing on the ultrasound image.

The weighting also slightly increases the noise floor in the direction of the projection. At deeper depths where shadowing is less in FIG. 3, the reduction in shadowing introduces an artifact. This may be acceptable or may be counteracted. By including more transform data in the creation of the projection image, the effect may be reduced. For example, data from a greater range of angles is selected for transforming back to the spatial domain. In another example, the formation of the weights or the projection image is processed so that the weights vary to account for shadow more greatly in the near field and less greatly in the far field. In either example approach, the weighting is to a lesser extent (i.e., closer to 1.0) for deeper locations along the imaging angles than for shallower locations.

The weighting of one frame is independent of the weighting of another frame. The weights may be the same or similar, but are derived from the data of the frame being weighted rather than from other frames. In alternative embodiments, the weights are a function of information from more than one frame of data.

In act 60, the weighted component frames of data are compounded together. The weighting and compounding may be performed as part of a same finite impulse response filtering. The processor or ultrasound system performs steered spatial compounding of the component frames for ultrasound imaging. The component frames may be low pass filtered or otherwise processed before combination.

The component frames include data representing specific locations. Where the frames of data represent the same locations or grid, the values from each frame representing a given location are combined. In one embodiment, detected and scan-converted frames of data are compounded together. Since scan-converted information is used, the data of each of the component frames are in a same format and grid pattern or spatial location sampling. Where the frames of data represent sampling along different grids, a nearest neighbor or interpolation is used to select or calculate the values used to combine. If the data is compounded prior to scan conversion, interpolation, extrapolation or other processes are used to compound any data representing adjacent or similar but not identical spatial locations.

The combination is for each location. The frames of data represent the same locations in at least the overlap region. Each of the component frames are compounded together for spatial locations representing the display or overlap region. Different locations may be associated with different numbers of frames and corresponding values. For example, an image representing more than the overlap region is generated. Due to steering, fewer component frames represent locations outside of the overlap region of all of the component frames. Any number of component frames may be used to determine the value for a given location, such as all of the frames for the overlap region and fewer than all for other locations.

Linear combination and non-linear combination may be used. For example, a maximum selection is applied. In another example, an average is applied. Weighted averaging may be used, such as emphasizing one component frame over others due to steering angle or motion between component frames. The average may reduce the variance associated with noise. Other linear or non-linear techniques may be used.

A single combination is made for a spatially compounded image. A sequence of images may be generated. New component frames are acquired in act 50. Each combination is of different component frames than another combination. The component frames may be different by using a moving window, such that a given component frame is used in a plurality of combinations. The shadow reduction is performed once for each component frame. Since the component frame itself does not change, the same weighting to reduce shadows is applied to the frame for any combination. The same weighted component frame may be used for any combination. The information may be recalculated as needed even for previously used frames in other embodiments. Alternatively, each component frame is acquired for one combination and not used in other combinations. The compound frame is output from the compounding.

In act 62, an image is generated of the overlap region of the patient. The processor or display processor uses the compounded frame of data formed by combining the weighted component frames of data to generate an image. The compounded frame of values representing the locations in the patient is used to determine pixel or image values. The compounded values are mapped to display values. Scan conversion, if not previously performed, may format that compounded frame of data to the display.

A steered spatial compound image is generated. The image is of the overlap region, but may include other locations. The image is a spatial compounded image generated from combining views. Further processing may be used, such as spatially and/or temporally filtering the compounded frame of data. The image represents the patient, such as showing different tissue and other structures.

The shadow in the image may be reduced or eliminated due to weighting based on the projection. By accounting for the shadowing along the steering direction, any anatomy in the signal at the shadow locations is amplified, and the shadow is reduced. The resulting image may provide useful information about the patient not otherwise available or otherwise more difficult to identify.

Figure 6:
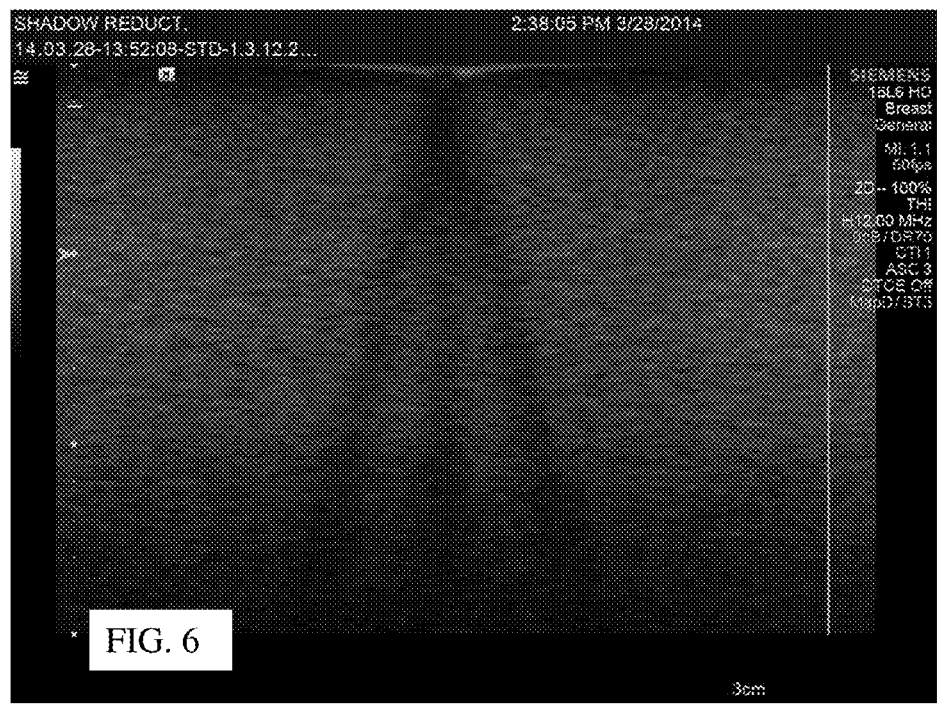
FIG. 6 is an example steered compound ultrasound image of a phantom with shadow artifacts from three component images.
Figure 7:
FIG. 7 is the example of the steered compound ultrasound image of FIG. 6 after suppression of shadows in the component images.

FIGS. 6 and 7 show images from steered compounding using three component frames with +15, 0, −15 degree linear steering. The images are of a tissue-mimicking phantom with shadow generated using a wire target at the surface of the phantom. In FIG. 6, the component frames are combined without shadow reduction. The shadow from each component frame along the respective steering direction is visible in the image from the compounded frame of data. In FIG. 7, shadow reduction individually or separately for each component frame is applied. The shadows in the compound image are reduced or eliminated.

Figure 8:
FIG. 8 is an example steered compound ultrasound image of a patient with shadow artifacts from three component images.
Figure 9:
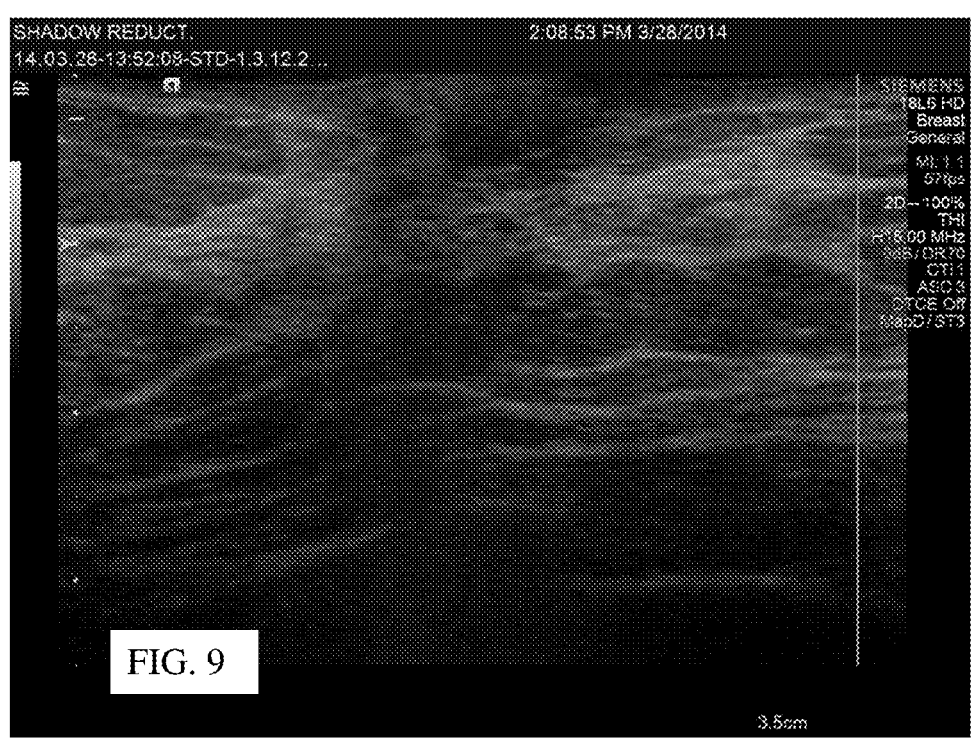
FIG. 9 is the example of the steered compound ultrasound image of FIG. 8 after suppression of shadows in the component images.

FIGS. 8 and 9 show images from steered spatial compounding using three component frames with +15, 0, −15 degree linear steering. The images are of a breast. The nipple commonly causes shadowing, and the images are of a common scan location of a plane with a nipple. As shown in FIG. 8, which does not include shadow reduction, this scanning area often has shadowing and requires the sonographer to use different scanning techniques to image the anatomy behind the nipple. Using the shadow reduction prototype and as shown in FIG. 9, the information behind the nipple from the other angular transmissions is enhanced, allowing the user to scan the area without significantly changing scanning technique.

FIG. 10 shows a system 10 for shadow suppression in ultrasound imaging. The system 10 is a medical diagnostic ultrasound system. In one embodiment, the system 10 is an automated breast volume scanner system with one or more transducers 14 for breast imaging. Breast imaging suffers from both the dense nipple causing shadowing as well as contact problems for the transducer 14 causing shadowing. Transducers 14 for imaging other locations with or without contact issues may be used. In alternative embodiments, all or part of the system 10 is a workstation or computer for processing or displaying medical images.

The system 10 provides steered spatial compounding, B-mode, flow mode, harmonic mode, M-mode, or other modes of scanning. In the embodiment discussed below, the steered spatial compounding mode is used. Similar components, such as using the same components without the compound processor 22 for B-mode, may provide other modes with shadow suppression. The system 10 includes a transmit beamformer 12, the transducer 14, a receive beamformer 16, a detector 18, a scan converter 20, the compound processor 22, a display 24, and a memory 26. Different, fewer or additional components may be provided. For example, an offline workstation implements the compound processor 22 and display 24 without the additional ultrasound acquisition components.

The transducer 14 comprises an one- or multi-dimensional array of piezoelectric, ceramic, or microelectromechanical elements. In one embodiment, the transducer 14 is a one-dimensional array of elements for use as Vector®, linear, sector, curved linear, or other scan format now known or later developed. For breast scanning, the array may be mounted to a tray allowing automated translation of the array to scan a volume of the breast. The array of elements has a wavelength, half wavelength, or other sampling frequency. A half-wavelength sampling of elements allows for greater steering angles, providing more spatial diversity for speckle reduction by compounding. The transducer 14 is adapted for use external to or use within the patient, such as a handheld probe, a catheter probe, or an endocavity probe. Multiple spatially distributed transducers or even scanning systems may be employed.

The transmit and/or receive beamformers 12, 16 operate as a beamformer. The beamformer is operable to acquire electronically or mechanically steered component frames of data responsive to different steering angles from a substantially same transducer position. The same scan pattern with different steering angles or different scan patterns resulting in different steering angles are used. Between two different scans, one or more scan lines may extend at a same angle from a same origin, but other scan lines are steered at different angles to provide component images responsive to different steering angles. For a given origin, at least one scan line may be at a different angle between the scans for two component frames of data. All or a majority of the scan lines may be steered differently for different frames.

The component frames of data represent different overlapping regions or a same region of the patient. The transducer 14 is substantially held in place for acquiring the component frames of data. "Substantially" is used to account for unintentional movement of the person holding the array, breathing or other motion caused by the patient, and any other incidental movement associated with using a probe not mounted in a fixed position relative to a patient fixed in place.

The transmit beamformer 12 is one or more waveform generators for generating a plurality of waveforms to be applied to the various elements of the transducer 14. By applying relative delays and apodizations to each of the waveforms during a transmit event, a scan line direction and origin from the face of the transducer 14 is controlled. The delays are applied by timing generation of the waveforms or by separate delay components. The apodization is provided by controlling the amplitude of the generated waveforms or by separate amplifiers. To scan a region of a patient, acoustic energy is transmitted sequentially along each of a plurality of scan lines. In alternative embodiments, acoustic energy is transmitted along two or more scan lines simultaneously or along a plane or volume during a single transmit event.

The receive beamformer 16 comprises delays and amplifiers for each of the elements in the receive aperture. The receive signals from the elements are relatively delayed and apodized to provide scan line focusing similar to the transmit beamformer 12, but may be focused along scan lines different than the respective transmit scan line. The delayed and apodized signals are summed with a digital or analog adder to generate samples or signals representing spatial locations along the scan line. Using dynamic focusing, the delays and apodizations applied during a given receive event or for a single scan line are changed as a function of time. Signals representing a single scan line are obtained in one receive event, but signals for two or more scan lines may be obtained in a single receive event. A component frame of data is acquired by scanning over a complete pattern with the beamformer. In alternative embodiments, a Fourier transform or other processing is used to form a component frame of data by receiving in response to a single transmit.

The detector 18 comprises a B-mode detector, Doppler detector or other detector. The detector 18 detects intensity, velocity, energy, variance or other characteristic of the signals for each spatial location in the component frame of data.

The scan converter 20 comprises a processor, filter, application specific integrated circuit or other analog or digital device for formatting the detected data from a scan line format (e.g., polar coordinate format) to a display or Cartesian coordinate format. The scan converter 20 outputs each component frame of data in a display format. The component frames may include values for locations representing regions outside of the display region.

The compound processor 22 comprises one or more memories, processors, control processors, digital signal processors, application specific integrated circuits, field programmable gate arrays, filters, multiplexers, buffers, multipliers, adders, lookup tables, or combinations thereof. In one embodiment, the compound processor 22 comprises a personal computer, motherboard, separate circuit board or other processor added to an ultrasound system for image processing using transfers of data to and from the ultrasound image generation pipeline or processing path (i.e. receive beamformer 16, detector 18, scan converter 20 and display 24). In other embodiments, the compound processor 22 is part of the image generation pipeline.

Using software, hardware, or combinations thereof, the compound processor 22 is configured to reduce shadows represented in one or more frames of data. Each frame of data, such as each component frame of data for steered spatial compounding, is processed individually or using just scan data for that frame to reduce shadow in the frame.

The compound processor 22 is configured to project the data of the frame to reduce along one dimension or along the steering direction(s) used to acquire the frame. The transmit or receive scan lines or lines with a same format are used in the projection. Data along each of the lines is combined, such as reducing a two-dimensional data field to one dimension. In one embodiment, the projection is a sum along the steering angles. The sum may be used alone or for an average. Since the projection is used to weight a frame of data representing locations in two-dimensions, the projection is expanded into a two-dimensional field of weights. For example, the average or sum along each scan line or line is copied as a weight for all of the locations along the respective scan line.

In another embodiment, the compound processor 22 is configured to project with a two-dimensional Fourier or other transform. The frame of data is transformed into the frequency domain. In the k-space, data is selected to form the projection image. For example, data along a lateral frequency axis corresponding to the steering angle or ranges of angles about the steering angle is selected. By applying the inverse transform on the selected data, the compound processor 22 creates a two-dimensional projection image or field of weights.

The compound processor 22 creates the weights from the one-dimensional projection or the projection image. The weights are set equal to or mapped to a range of values linearly based on the magnitudes of the projection image. In other embodiments, a non-linear relationship between projection magnitude and weights is used. Using a look up table or calculations, the compound processor 22 determines the weight for each location represented by the frame of data.

The compound processor 22 may select data for inverse transform, process any projection, and/or process the weights. For example, the weights or projection before expansion are low pass filtered. As another example, data in the frequency domain is selected or the weights are altered to vary the weighting as a function of depth or along the steering angle.

The compound processor 22 weights the frame of data. The weights are set so that the shadow region is amplified relative to non-shadow regions. The locations along steering angles associated with less intensity are increased by the weights. Other locations are maintained the same, but may be increased or decreased to a lesser extent than the shadow locations. The weights are applied by multiplication, but addition, division, subtraction, or other functions may be used. The weights or the application of the weights may be thresholded, such as applying no weights or weight of 1.0 for any weights or magnitude of the projection image within a percentage or range about an average weight of magnitude for the frame. Weights or magnitudes greater than the threshold difference from average are more likely associated with shadow, so are applied without normalizing to 1.0.

The compound processor 22 is configured to generate a compound image from the weighted steered frames of data. The compound processor 22 is configured to combine or compound one or more component frames of data representing at least a same region for display. For example, the compound processor 22 has a memory and multiplier for each of the component frames for weighting and an adder connected to each of the multipliers for combining signals representing a given spatial location from each of the component frames of data in a finite impulse response filter format. Linear or non-linear combinations of component frames of data may be provided, such as averaging or selecting a maximum signal. The resulting compounded data is used to generate the image.

The compound processor 22 is configured to combine detected and scan converted data. In alternative embodiments, the compound processor 22 is positioned between the detector 18 and scan converter 20 for combining detected but not scan converted data, positioned prior to a log compressor of the detector 18 for combining non-compressed information or positioned prior to the detector 18. Any of various embodiments for combining multiple data representing the same region or combining component frames of data may be used.

In one embodiment, the compound processor 22 includes an image display plane or memory for each of the component frames, such as six display planes. Each display plane has foreground and background pages for allowing simultaneous writing to memory while reading out from memory, but other memory structures may be provided. The memory stores information for each spatial location, such as flow mode or Doppler mode parameter data, B-mode data, a color pan box information and the display region border information. A filter responsive to different multiplier coefficients combines the component frames using different functions based on the contribution (i.e., weighting). A lookup table provides the different weighting coefficients to the multipliers or the weights are calculated. Different coefficients may also be provided for combining different numbers of component frames.

The instructions for implementing the processes, methods and/or techniques discussed above are provided on non-transitory computer-readable storage media or memories 26, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 24 is a CRT, monitor, flat screen, LCD, projection or other display for displaying the compounded ultrasound image. During the display refresh, the component frames are read, a projection or projection image formed, weights determined from the projection image or projection, the component frames weighted, and the weighted component frames compounded to generate the image on the display 24. Display plane memories are used for each component frame of data. The resulting frame of data is a compound image responsive to component frames of data. Different locations have values from different component frames or from multiple or all of the component frames. The display image format or display region is trapezoidal, trapezoidal like, rectangular, sector, pie shaped, Vector® or other shape. The compound image is updated in real-time, such as updating the compound image as each new component frame of data is acquired and a previous component frame of data is removed from a previous compound image or is removed from a buffer for compounding the next compound image. Alternatively, real-time compounding is provided by compounding different sets of component frames of data with no or few component frames used in common for each set. In yet other alternative embodiments, offline or non-real time compounding is provided.

The display 24 is operable to display a compound image responsive the component frames of data. The compound image reduces speckle while maintaining signal-to-noise ratio. The combined frame of data is displayed as the compound image. Component frames of data may be used to generate images without compounding.

In an alternative embodiment, compounding is performed in three or four-dimensional imaging. Component frames of data are acquired with different lateral as well as elevation steering angles. The projections along the steering angles are used to create a three-dimensional weight field for weighting the component frames.

While the invention has been described above by reference to various embodiments, it should be understood that many changes and modifications can be made without departing from the scope of the invention. While the description herein provides examples of steered spatial compounding, other compounding, such as temporal or frequency compounding, may alternatively or additionally be used. Steering may be relative to the transducer (e.g., beamformer steering) and/or relative to the location being scanned (e.g., insonifying from different directions with or without beamformer steering). It is therefore intended that the foregoing detailed description be regarded as illustrative rather than limiting, and that it be understood that it is the following claims, including all equivalents, that are intended to define the spirit and scope of this invention.

We claim:

1. A method for shadow suppression in ultrasound imaging, the method comprising:
    acquiring, with a transducer, steered component frames of data, the steered component frames of data representing an overlap region of a patient and being responsive to different imaging angles;
    for each of the steered component frames of data, projecting, by a processor, the data along the respective imaging angle into a projection, the projecting collapsing the data along each scan line of the imaging angle into a value for each of the scan lines, the combined values across the scan lines showing a variation in intensity of the shadow by lateral position of the steered component frame of data;
    spatially weighting the steered component frames of data by kernels that are a function of the values of the respective projections of the scan lines, the function weighting the steered component frames of data per scan line, the spatially weighting by the kernels suppressing the shadows in the steered component frames of data;
    compounding, by the processor, the weighted component frames of data together; and
    generating an image of the overlap region of the patient from a result of the compounding.

2. The method of claim 1 wherein acquiring comprises scanning along scan lines where a majority of the scan lines for each steered component frame of data are at a same angle to the transducer and the angle is different for the different steered component frames of data.

3. The method of claim 1 wherein projecting comprises summing the data of the steered component frames of data along the imaging angles.

4. The method of claim 1 wherein projecting and weighting comprise projecting and weighting each of the steered component frames of data independently of each other.

5. The method of claim 1 wherein projecting comprises transforming into a k-space.

6. The method of claim 5 wherein projecting comprises applying a Fourier transform.

7. The method of claim 1 further comprising:
    expanding the projection along the imaging angles into a two-dimensional field; and
    forming the kernel from the two-dimensional field.

8. The method of claim 1 wherein weighting comprises weighting to a lesser extent by variation in weight values for deeper locations along the imaging angles than for shallower locations.

9. The method of claim 1 further comprising:
creating transform projection images from the projections; and
forming the transform projection images into the kernels.

10. The method of claim 9 wherein creating comprises creating such that the kernel varies with depth along the imaging angles.

11. The method of claim 9 wherein forming comprises mapping the transform projection images to weights forming the kernels, the mapping being a linear or non-linear relationship.

12. The method of claim 1 wherein weighting comprises weighting with the kernel comprising weights set for each location of the frames of data.

13. The method of claim 1 wherein generating the image comprises generating a steered spatial compound image.

14. A non-transitory computer readable storage medium having stored therein data representing instructions executable by a programmed processor of an ultrasound system for shadow suppression in ultrasound imaging, the storage medium comprising instructions for:
weighting with spatial weights at least one component frame of a plurality of component frames for spatial compounding, the weighting of the one component frame being independent of the others of the component frames, the weighting reducing the shadows where the spatial weights include spatial variance in an amount of the reducing, the spatial variance of the spatial weights for the at least one of the component frames being different than for another of the component frames due to difference in the shadows;
steered spatial compounding the component frames, by the ultrasound system, for ultrasound imaging.

15. The non-transitory computer readable storage medium of claim 14 wherein weighting comprises:
projecting along transmit angle directions in the component frames, each of the component frames having different transmit angle directions than others of the component frames;
determining the spatial weights for spatial locations of the component frames from results of the projecting for the respective component frames; and
weighting, with the spatial weights, the component frames prior to the compounding.

16. The non-transitory computer readable storage medium of claim 14 wherein weighting comprises:
transforming the at least one component frame into a two-dimensional frequency domain; and
determining the spatial weights from results of the transforming.

17. The non-transitory computer readable storage medium of claim 14 wherein weighting independently comprises determining the spatial weights for each of the component frames using data of the respective component frame without information from others of the component frames.

18. A system for shadow suppression in ultrasound imaging, the system comprising:
a beamformer operable to acquire a sequence of steered frames of data responsive to different steering angles from a substantially same transducer position and representing an overlap region;
a processor configured to project the steered frames of data along the steering angles into projections, the projections used to form projection images having a same value for each depth of each scan line of the steering angles and different values by scan line, weight the steered frames of data as a function of the projection images, and generate a compound image from the weighted frames of data; and
a display operable to display the compound image.

19. The system of claim 18 wherein the processor is configured to project with a two-dimensional Fourier transform, the projections being in a frequency domain along lateral frequency axes corresponding to the steering angles.

* * * * *